US012564445B2

(12) United States Patent
Masaki et al.

(10) Patent No.: US 12,564,445 B2
(45) Date of Patent: Mar. 3, 2026

(54) METHODS FOR OPERATING A MEDICAL CONTINUUM ROBOT

(71) Applicants: Canon U.S.A., Inc., Melville, NY (US); The Brigham and Women's Hospital Incorporated, Boston, MA (US)

(72) Inventors: Fumitaro Masaki, Brookline, MA (US); Nobuhiko Hata, Newton, MA (US); Franklin King, Allston, MA (US); Takahisa Kato, Brookline, MA (US)

(73) Assignees: Canon U.S.A., Inc., Melville, NY (US); The Brigham and Women's Hospital Incorporated, Boston, MA (US)

( * ) Notice: Subject to any disclaimer, the term of this patent is extended or adjusted under 35 U.S.C. 154(b) by 380 days.

(21) Appl. No.: 18/019,063

(22) PCT Filed: Aug. 5, 2021

(86) PCT No.: PCT/US2021/044787
§ 371 (c)(1),
(2) Date: Jan. 31, 2023

(87) PCT Pub. No.: WO2022/031995
PCT Pub. Date: Feb. 10, 2022

(65) Prior Publication Data
US 2023/0277245 A1    Sep. 7, 2023

Related U.S. Application Data

(60) Provisional application No. 63/181,840, filed on Apr. 29, 2021, provisional application No. 63/062,076, filed on Aug. 6, 2020.

(51) Int. Cl.
*A61B 1/01*       (2006.01)
*A61B 1/005*       (2006.01)
(Continued)

(52) U.S. Cl.
CPC .............. *A61B 34/10* (2016.02); *A61B 34/30* (2016.02); *A61B 2034/107* (2016.02); *A61B 2034/301* (2016.02)

(58) Field of Classification Search
CPC .............. A61B 34/10; A61B 2034/105; A61B 2034/107; A61B 2034/301; A61B 2017/00809
See application file for complete search history.

(56) References Cited

U.S. PATENT DOCUMENTS 6,727,963 B1    4/2004  Taniguchi et al.
2004/0209234 A1   10/2004  Geiger
(Continued)

FOREIGN PATENT DOCUMENTS

JP    2007-509649 A    4/2007
JP    2011-189074 A    9/2011
(Continued)

OTHER PUBLICATIONS

J. D. Gibbs, et al., Optimal Procedure Planning and Guidance System for Peripheral Bronchoscopy. IEEE Transactions on Biomedical Engineering, vol. 61, No. 3, Mar. 2014.

*Primary Examiner* — Boniface N Nganga
(74) *Attorney, Agent, or Firm* — Canon U.S.A., Inc., IP Division

(57)    ABSTRACT

The subject disclosure is directed to methods for using an articulated medical device in treating a subject or patient, wherein the device is capable of maneuvering within the subject or patient, and the method is capable of assessing multiple pathways for reaching a desired target and assigning a difficulty score to each the various pathways.

22 Claims, 13 Drawing Sheets

(51) Int. Cl.
  A61B 34/10  (2016.01)
  A61B 34/30  (2016.01)

(56)            References Cited

U.S. PATENT DOCUMENTS

| 2018/0240237 | A1 | 8/2018 | Donhowe et al. |
| 2018/0296282 | A1 | 10/2018 | Kose et al. |
| 2019/0105468 | A1 | 4/2019 | Kato et al. |

FOREIGN PATENT DOCUMENTS

| JP | 2019093119 | A | 6/2019 |
| WO | 2012/151585 | A2 | 11/2012 |
| WO | 2018/204202 | A1 | 11/2018 |

Base of the Proximal Section

------------- The Computed Shape of the Distal Section of the Robotic Bronchoscope

- - - - - - The Computed Shape of the Middle Section of the Robotic Bronchoscope

- - - - - - The Computed Shape of the Proximal Section of the Robotic Bronchoscope ——————— Centerline of the Airway ◄————► Deviation ◄- - - - - Direction of the tip of the Distal Section ◄——————— Tangential Line of the Centerline ——————► Offset Offset

Difficulty Score for Design 1

Difficulty Score for Design 2

Difficulty Score

Difficulty Score for Design 3

METHODS FOR OPERATING A MEDICAL CONTINUUM ROBOT

CROSS REFERENCE TO RELATED PATENT APPLICATIONS

This application claims priority from U.S. Provisional Patent Application No. 63/062,076 filed on Aug. 6, 2020, and U.S. Provisional Patent Application No. 63/181,840 filed on Apr. 29, 2021, both in the United States Patent and Trademark Office, the disclosures of which are incorporated herein in their entirety by reference.

FIELD OF DISCLOSURE

The present disclosure relates generally to methods for operating an articulated medical device, wherein the device is capable of maneuvering within a subject/patient. The methods of operating the medical device are centered around selecting and evaluating one or more pathway for advancing the medical device through the subject/patient to the end target. More specifically, the subject disclosure details methods and apparatus for advancing the medical device through the ever-changing anatomy of a subject/patient, while taking into consideration the least tortuous and safest pathway for reaching the target.

BACKGROUND OF THE DISCLOSURE

Articulated medical devices generally include one or more control mechanisms located at a proximal end of the medical device configured to enable remote manipulation of the device.

In order to facilitate articulation of these medical devices, continuum robots are used in clinical cases, especially to articulate around/through organs with tortuous structures, such as the airway of the lung and blood vessel. Clinical studies have shown that robotic bronchoscope can reach higher generation of the airway of the lung than a conventional manual bronchoscope. In addition, a navigation bronchoscopy system, which combines electromagnetic navigation systems with respiratory gating technology, further improve efficacy and use, and allows for the system to display the shape of the airway based on respiratory motion.

In order to control a continuum robot with multiple articulating sections, follow-the-leader ("FTL") motion is widely used. In FTL, an operator only controls the leading section of the continuum robot, allowing and the remainder of articulating sections to automatically follow in the path of the leading section.

At present, the existing art assesses the difficultly of advancing the conventional bronchoscopy (manual bronchoscope) into the tortuous pathway of the subject by considering the diameter of the airway and the bronchoscope, as well as the angle of bifurcation points and maximum angle of the bronchoscope.

However, the existing art doesn't take into account the shape of the flexible shaft of the bronchoscope in assessing the difficulty of bronchoscopy. This is critical for robotic bronchoscopy, and under the constant-curvature model of a continuum robot, the ideal shape of a section of the continuum robot is an arc, which doesn't always translate to the shape of the passageway.

To assess the difficulty of robotic bronchoscopy, assessing how well the shape of the entire body of the robotic bronchoscope fits the shape of the passageway is important, and could lead to a less invasive procedure.

In addition, the existing art is also capable of predicting how deep the bronchoscope can be inserted into the subject, but there is no alternative option or paths to increase the chances of reaching the target location, or remapping the path to reach the target with less intrusion and/or uncomfort to the patient.

Accordingly, advancement in methods of operating a medical device are necessary and warranted, to reduce unnecessary uncomfort in the patient, and increase the likelihood of reaching the target less invasively.

SUMMARY

Thus, to address such exemplary needs in the industry, the present disclosure teaches methods for using a bendable medical apparatus comprising: providing a computed tomography image of a subject; providing a bendable medical apparatus comprising: an actuation unit; a bendable body which is bendable by the actuation unit; and a controller configured to send a control signal to the actuation unit for bending the bendable segment; mapping a pathway for the bendable body based on the computed tomography image of a subject; determining a deviation of the pathway for the bendable body from a centerline of the mapped pathway; and assigning a difficulty score for the pathway based on a level of deviation of the pathway.

Furthermore, the subject disclosure also teaches a method for treating a subject, comprising: providing a computed tomography image of the subject; providing a bendable medical apparatus comprising: an actuation unit; a bendable body which is bendable by the actuation unit; and a controller configured to send a control signal to the actuation unit for bending the bendable segment; mapping a pathway for the bendable body based on the computed tomography image of a subject; determining a deviation of the pathway for the bendable body from a centerline of the mapped pathway; assigning a difficulty score for the pathway based on a level of deviation of the pathway; and using the difficulty score to determine, in part, how the subject will be treated; and treating the subject with the bendable medical apparatus.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

3

Figure 3:
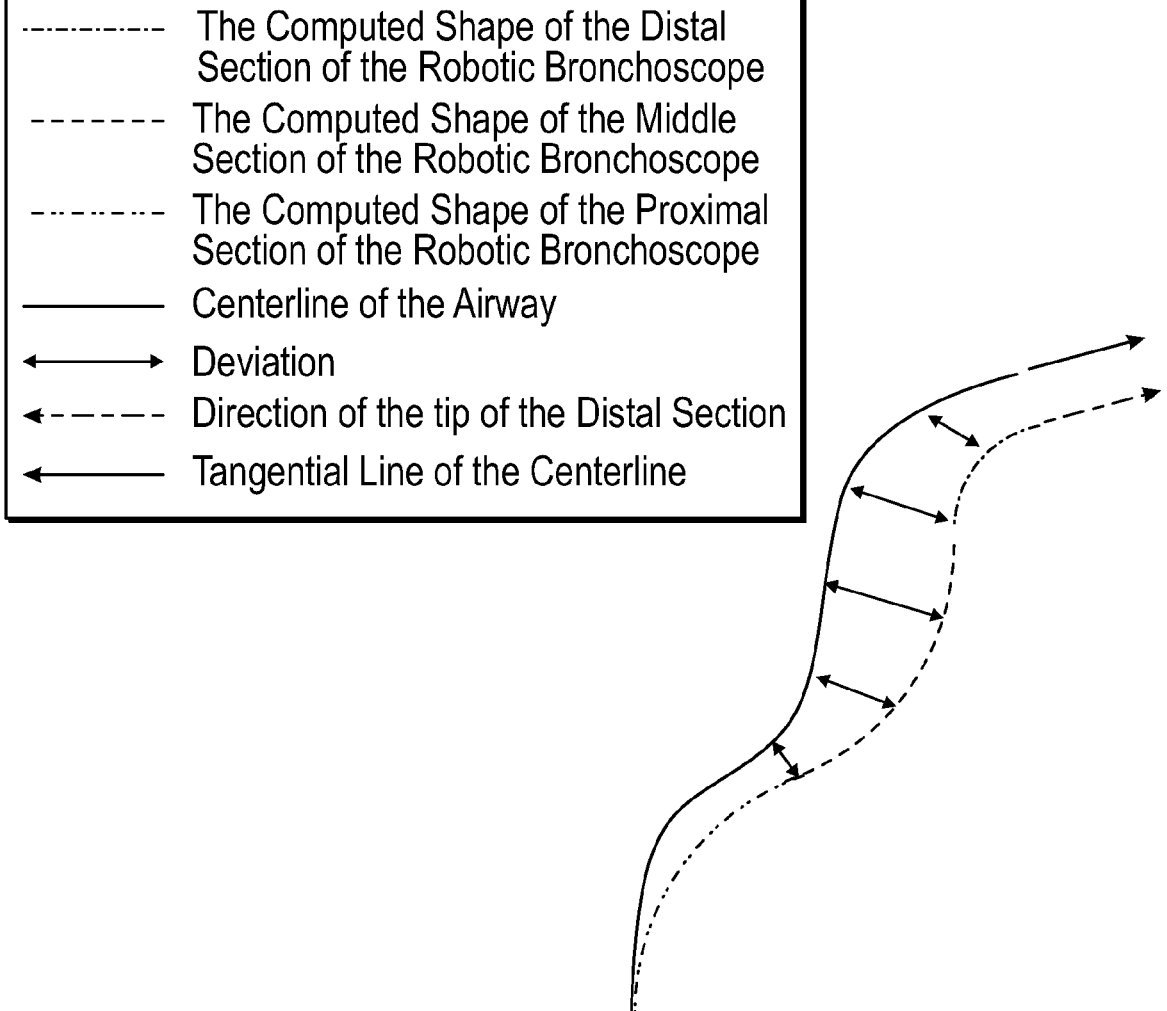

FIG. 3 illustrates an exemplary path for the robotic medical device, according to one or more embodiments of the present subject matter.

Figure 4:
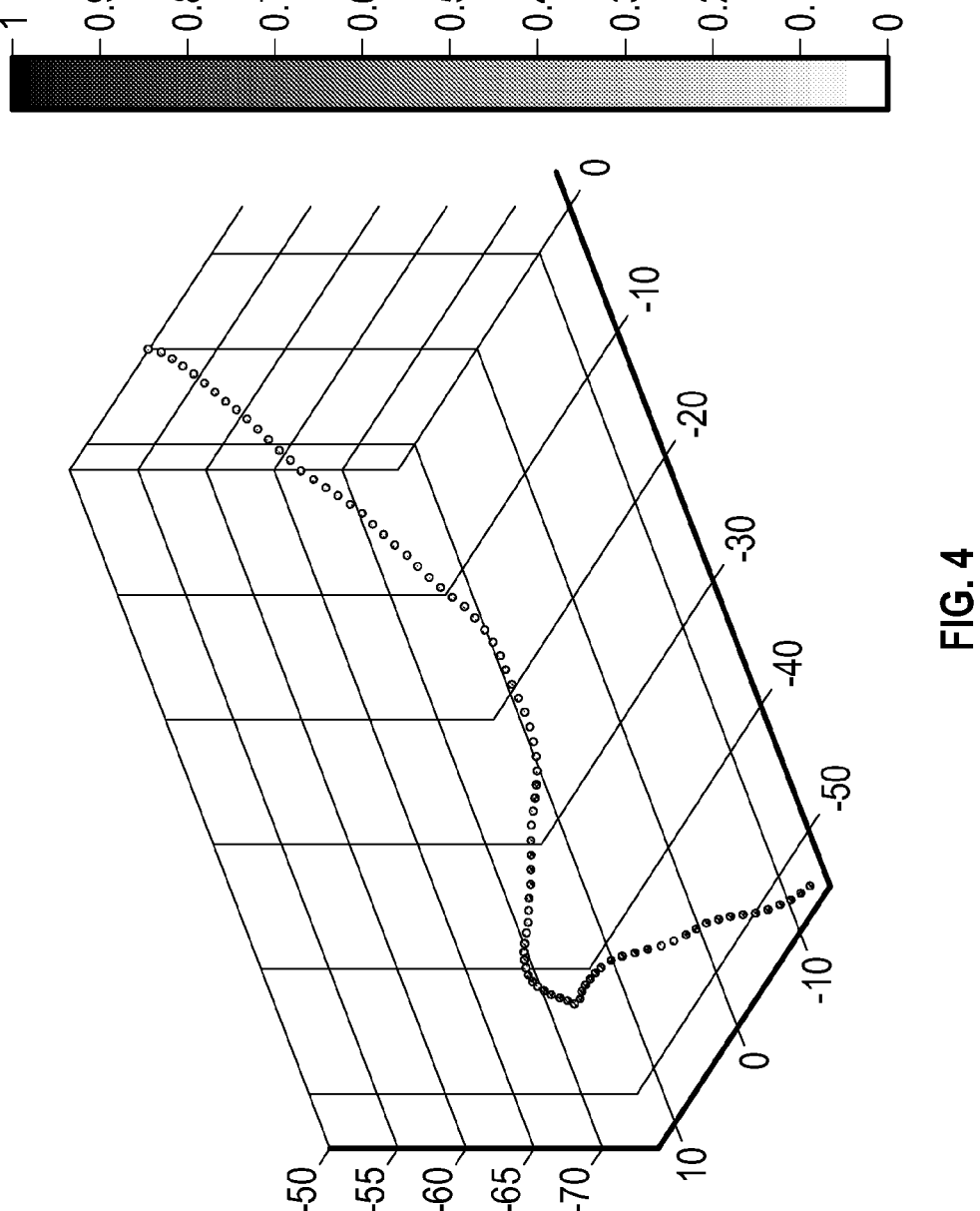

FIG. 4 provides a graph representing a difficulty score for an exemplary path for the robotic medical device, according to one or more embodiments of the present subject matter.

Figure 5:
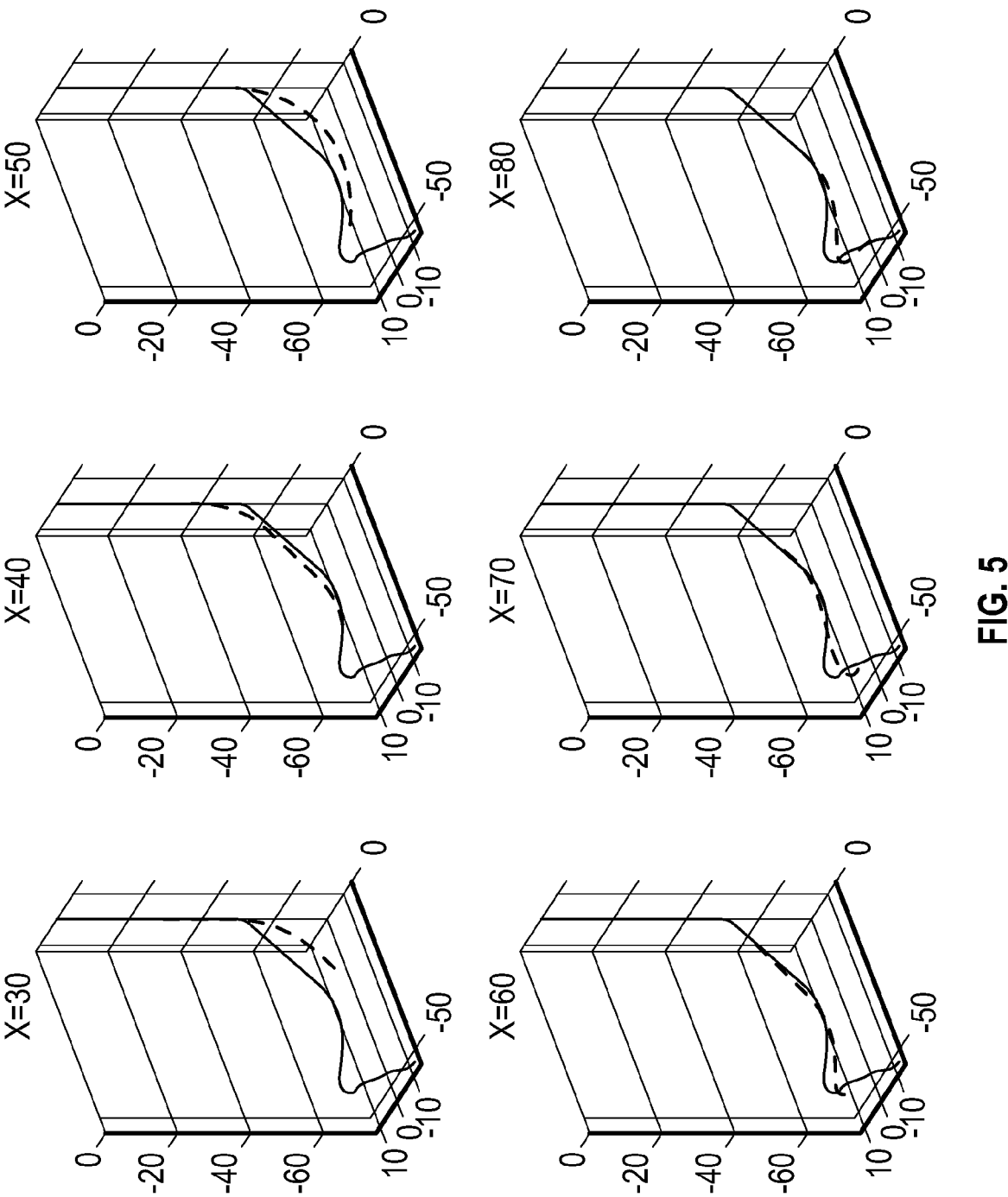

FIG. 5 illustrates chronological graphs depicting an exemplary path for the robotic medical device as the device progresses, according to one or more embodiments of the present subject matter.

Figure 6:
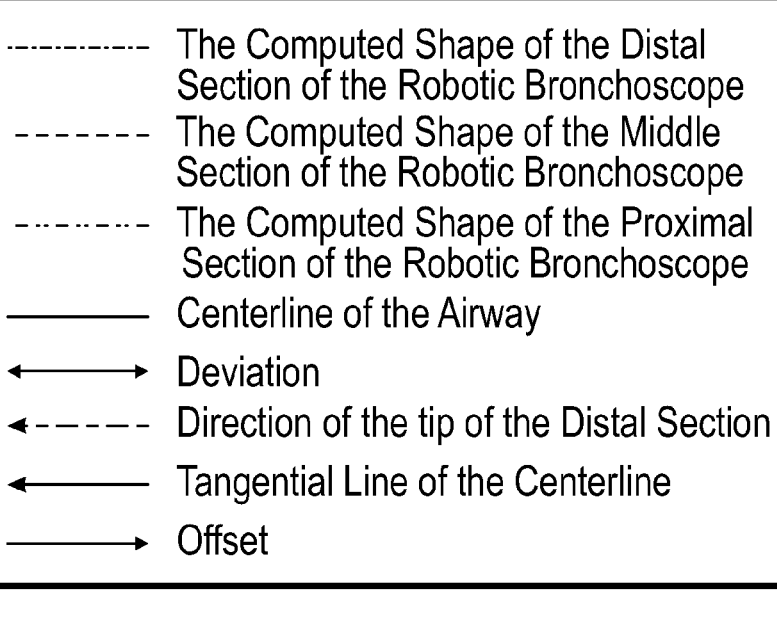

FIG. 6 illustrates an exemplary path for the robotic medical device, according to one or more embodiments of the present subject matter.

Figure 7:
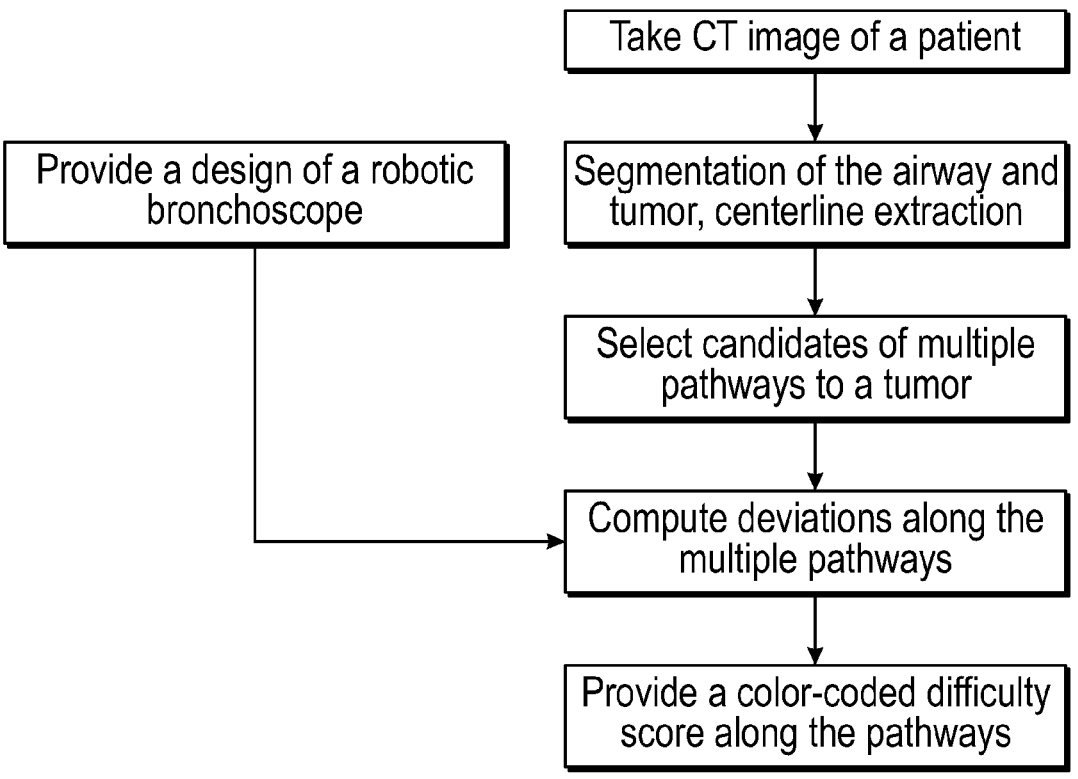

FIG. 7 is a flowchart depicting a method for employing the robotic medical device, according to one or more embodiments of the present subject matter.

Figure 8:
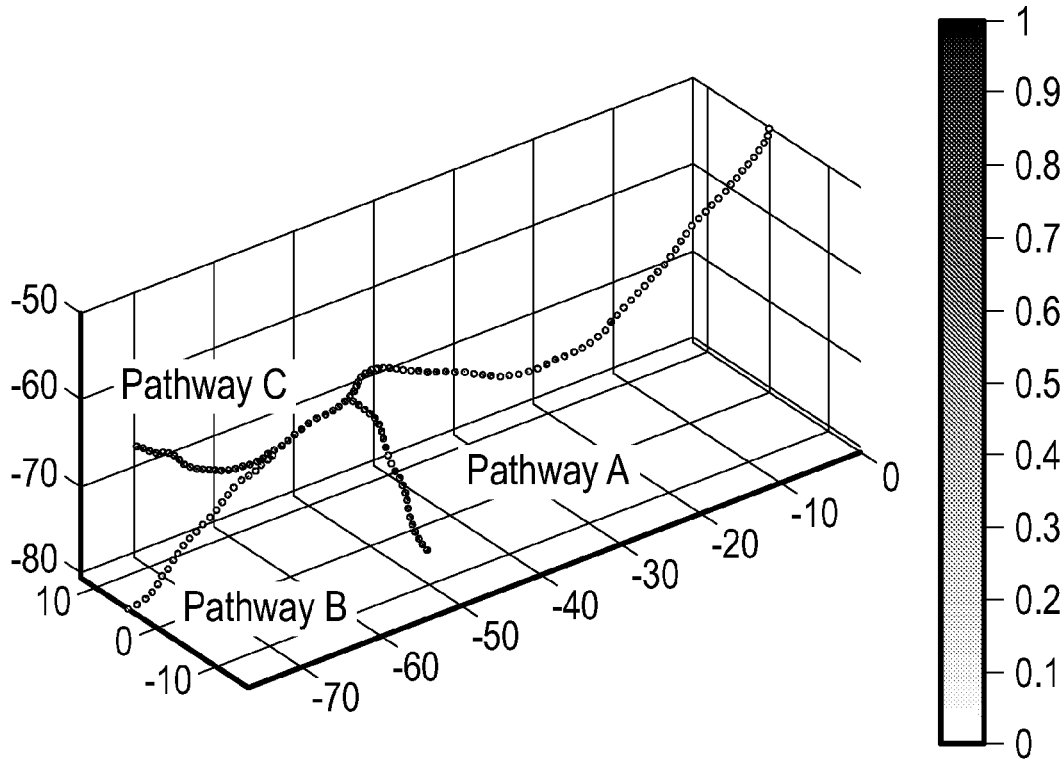

FIG. 8 provides a graph representing various difficulty scores associated with various exemplary paths for the robotic medical device, according to one or more embodiments of the present subject matter.

Figure 9:
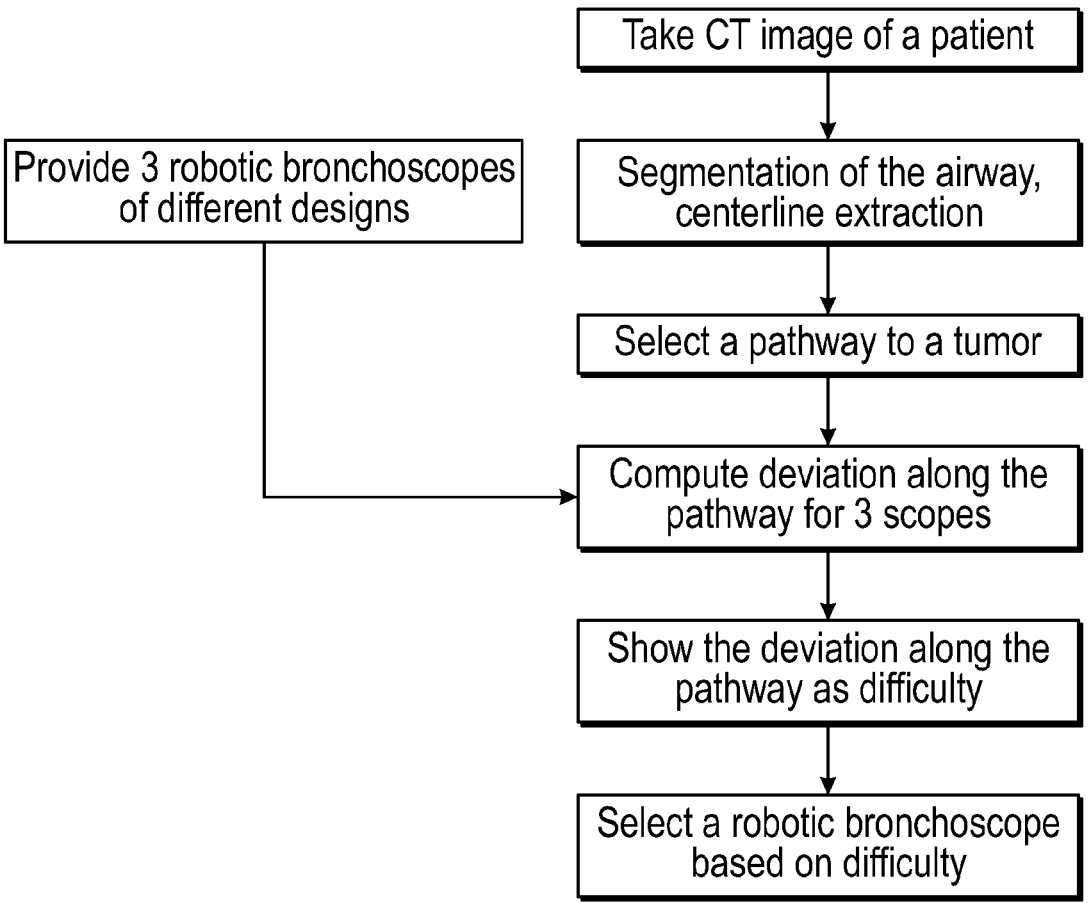

FIG. 9 is a flowchart depicting a method for employing the robotic medical device, according to one or more embodiments of the present subject matter.

Figure 10:
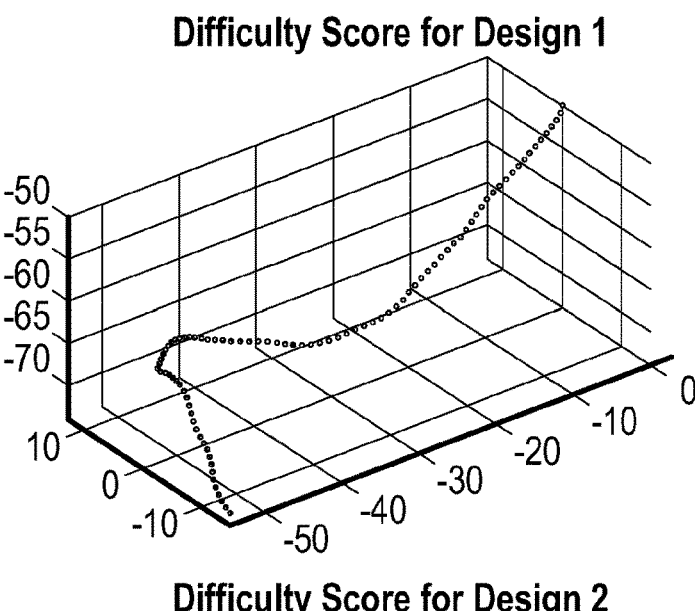
Figure 10:
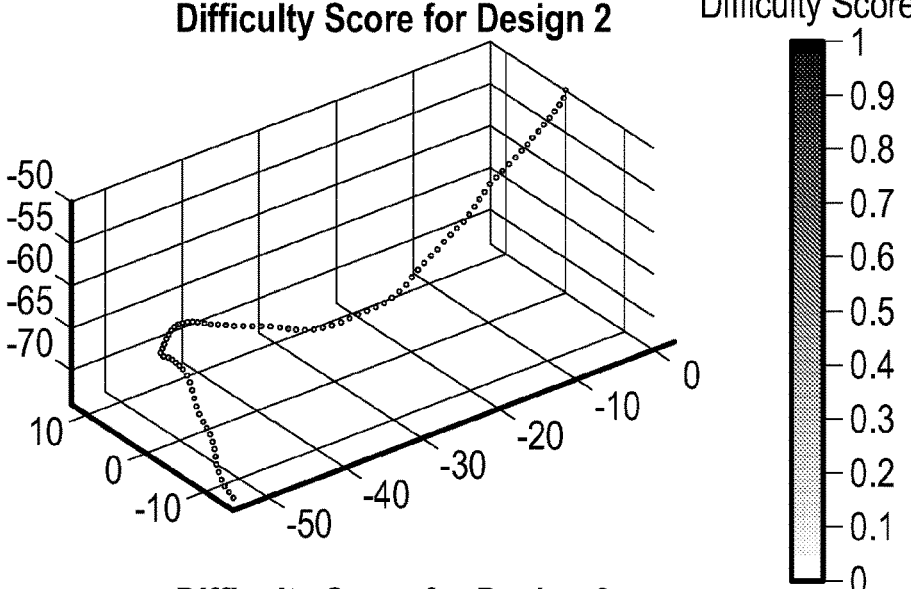
Figure 10:
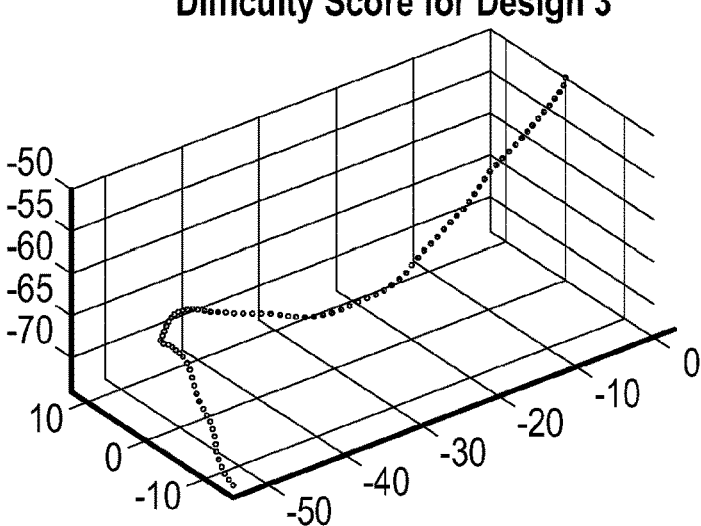

FIG. 10 provides various graphs depicting exemplary pathways for the robotic medical device as well as their associated difficulty scores, according to one or more embodiments of the present subject matter.

Figure 11:
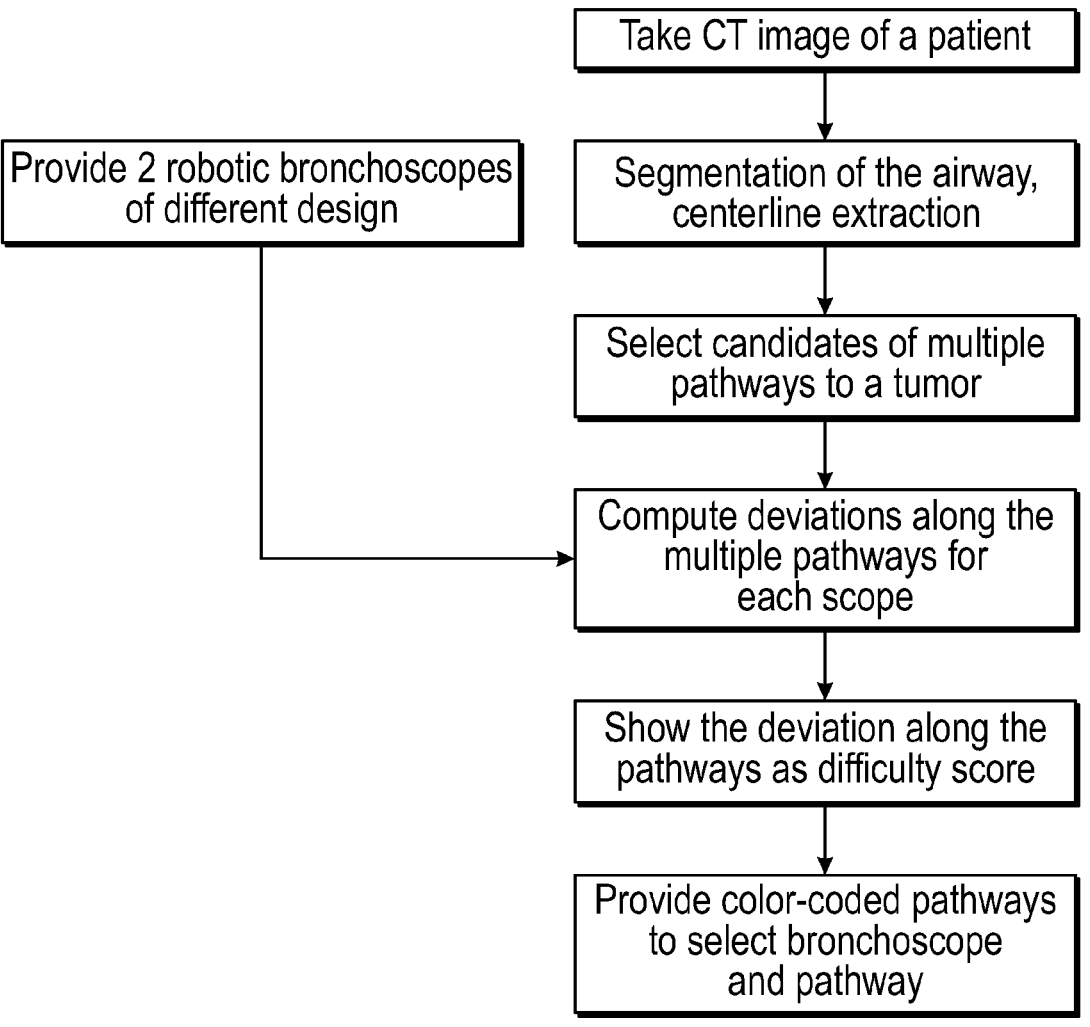

FIG. 11 is a flowchart depicting a method for employing the robotic medical device, according to one or more embodiments of the present subject matter.

Figure 12:
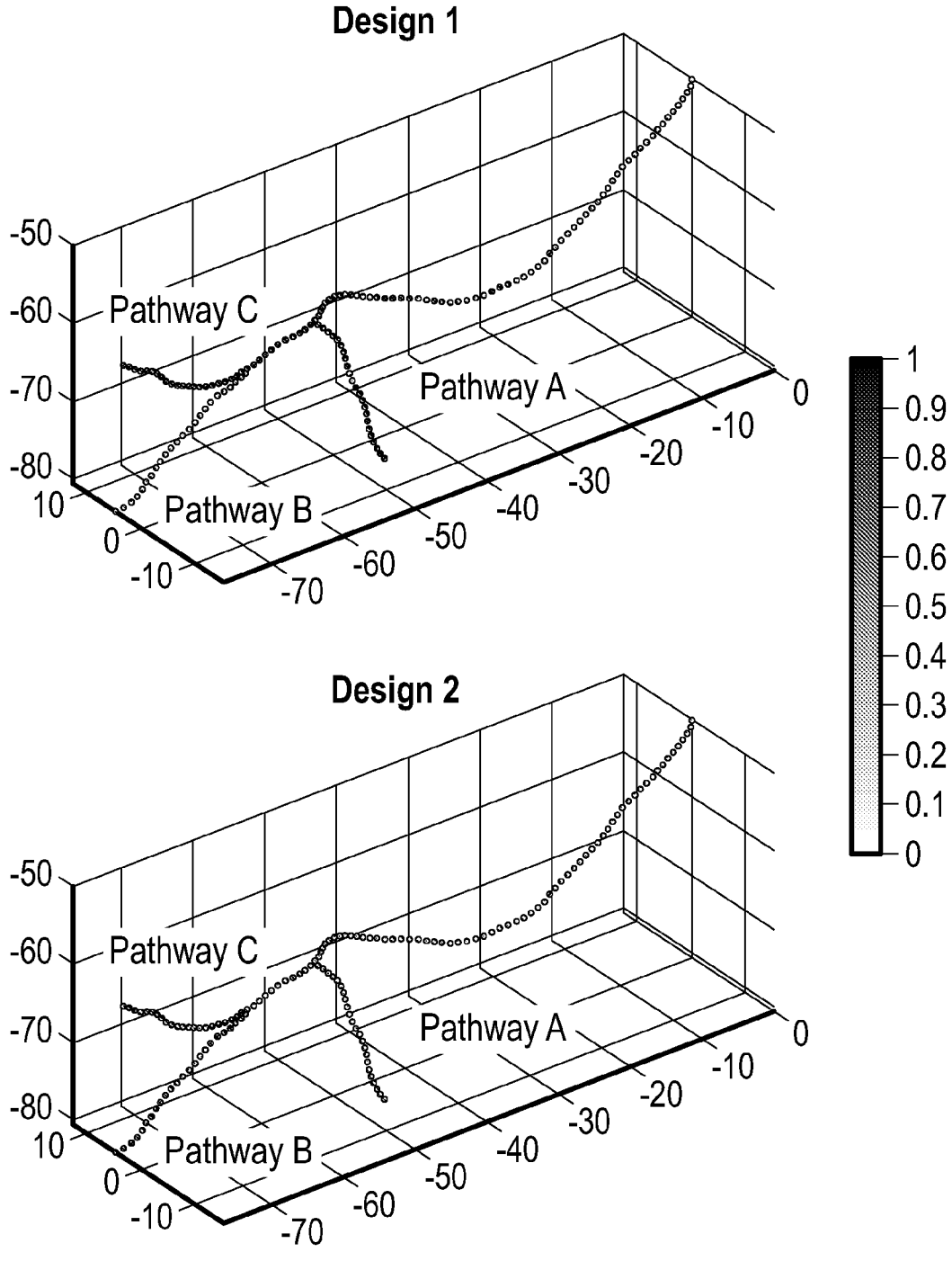

FIG. 12 provides two graphs depicting exemplary pathways for the robotic medical device as well as their associated difficulty scores, according to one or more embodiments of the present subject matter.

Figure 13:
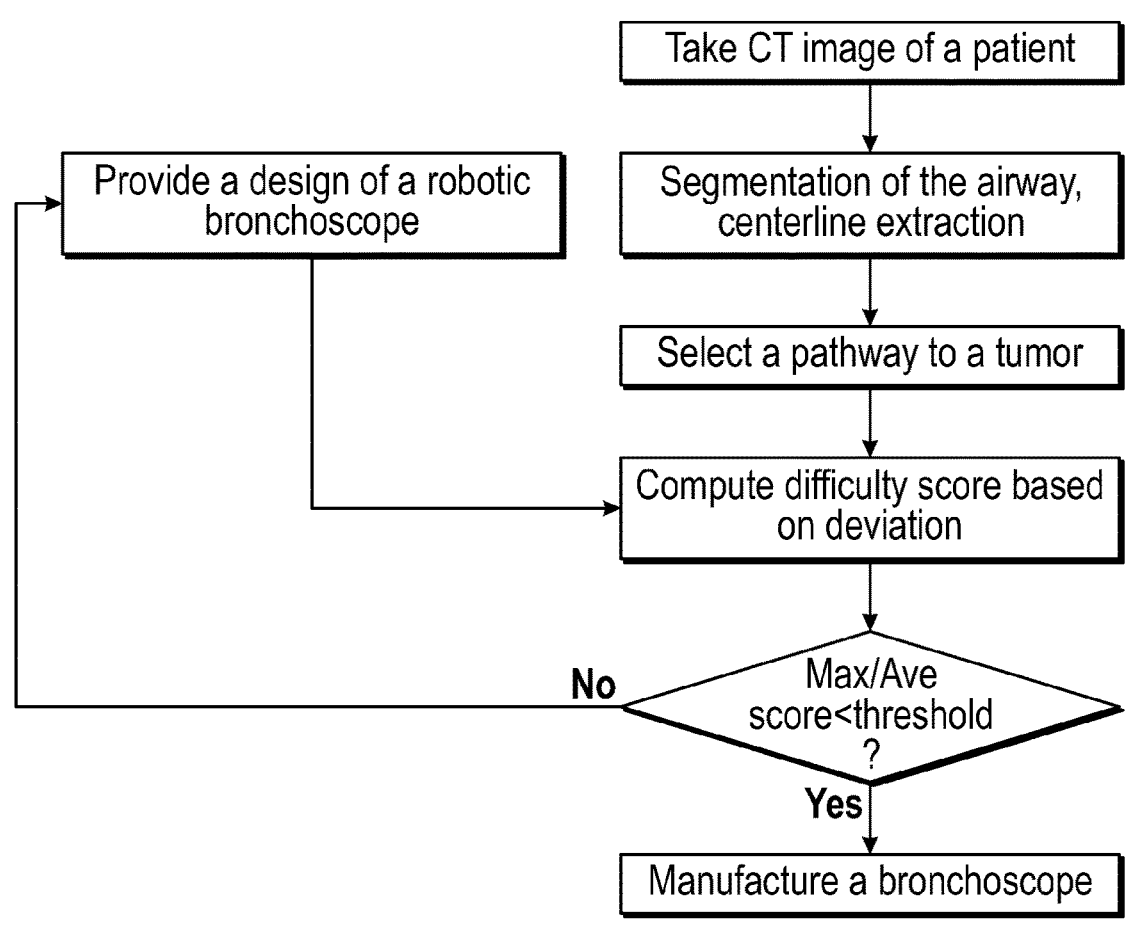

FIG. 13 is a flowchart depicting a method for employing the robotic medical device, according to one or more embodiments of the present subject matter.

Figure 14:
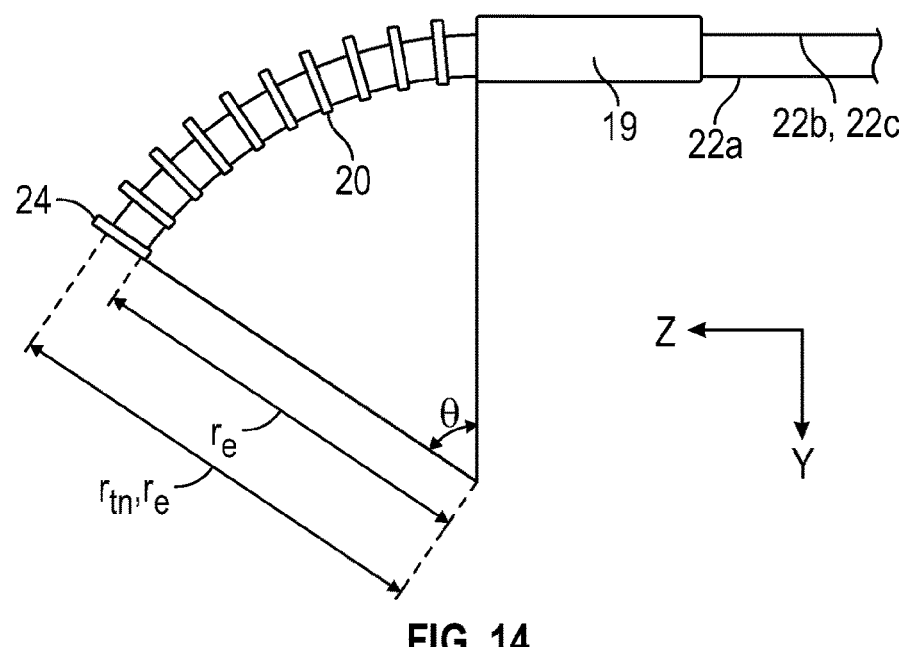

FIG. 14 a plan view showing deformation of the wire-driven manipulator when the linear member is driven according to one or more embodiments of the present subject matter.

Figure 15:
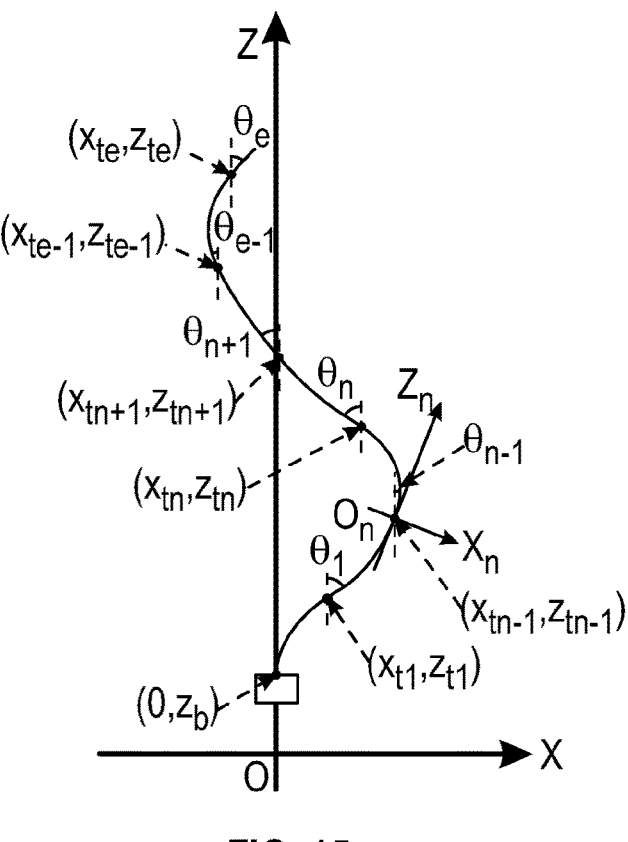

FIG. 15 illustrates a kinetic model according to one or more embodiments of the present subject matter.

Figure 16:
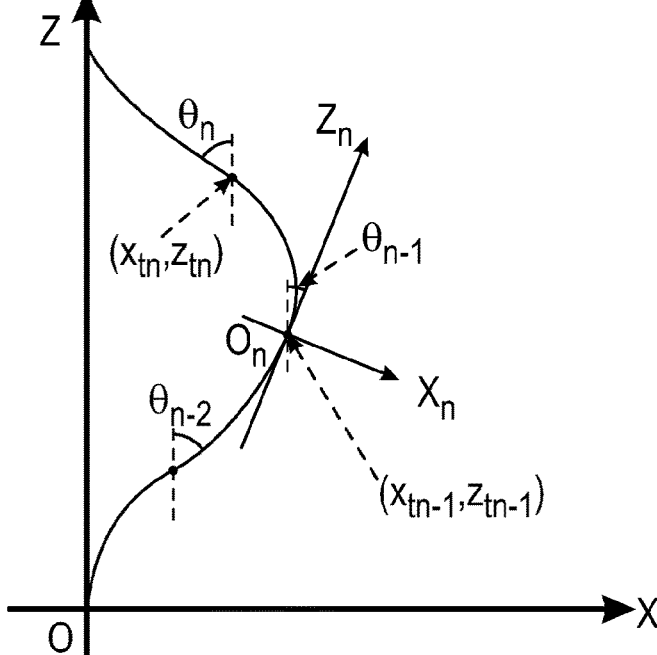

FIG. 16 illustrates a kinetic model according to one or more embodiments of the present subject matter.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings guidance device 10 herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

The present subject matter discloses methods for an articulated medical device configured to be guided into a patient or subject (hereafter used interchangeably) and articulated around/through organs and other elements within the patient to reach a desired destination. The methods are intended to go beyond planning a pathway to the desired destination, and determining which pathway is best suited for the given articulated medical device with the least amount of discomfort, harm or trauma to the patient.

Figure 1A:
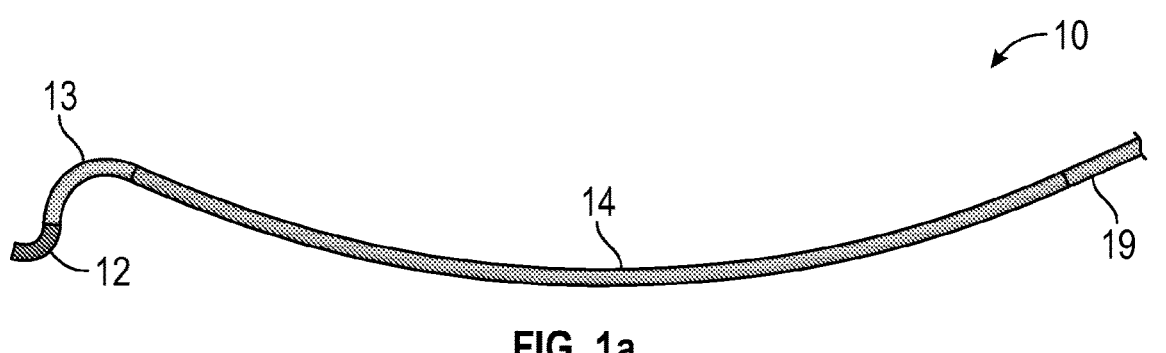
FIG. 1a provides an image of a robotic medical device, according to one or more embodiments of the present subject matter.
Figure 1B:
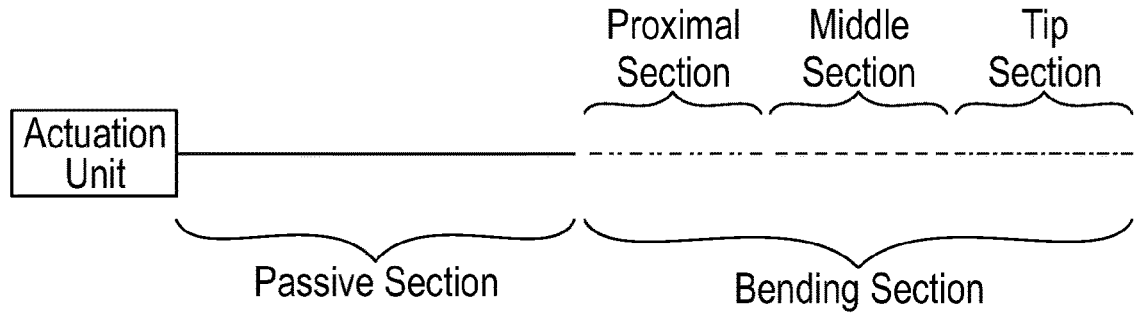
FIG. 1b illustrates the structure of a three-section robotic medical device, according to one or more embodiments of the present subject matter.

FIGS. 1*a* and 1*b* show the structure of a three-section robotic bronchoscope 10. The robotic bronchoscope 10 has a passive section 19 and a bending section 20, and the bending section 20 consists of three sections (distal section 12, middle section 13, and proximal section 14). The robotic bronchoscope is in communication with an actuation unit 11. In some embodiments, the actuation unit may be defined as a driving unit.

FIG. 1*a* is a side view of an example embodiment of a robotic bronchoscope 10, which includes a tool channel through both the passive section 19 and bending section 20. The tool channel has a substantially-cylindrical configuration. The clinical user can insert and retrieve a biopsy tool through the tool channel to the opening at the end of the distal section 12.

Figure 1C:
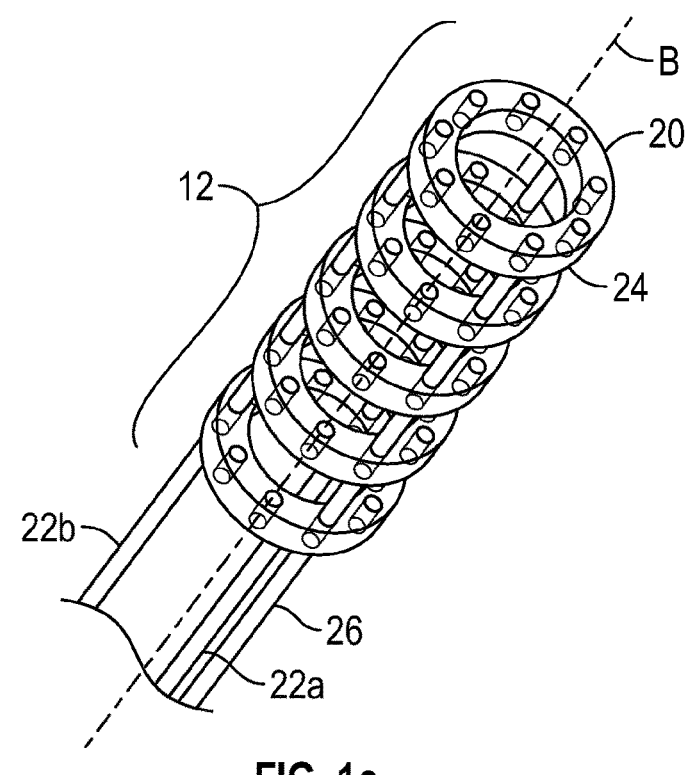
FIG. 1c illustrates a side perspective view of a structure of a three-section robotic medical device, according to one or more embodiments of the present subject matter.

FIG. 1*c* illustrates the guide rings 24 and the driving wires 22 of an example embodiment of a bronchoscope 10. FIG. 1*c* shows an exploded view of the bendable distal section 12, includes five guide rings 24, two driving wires 22*a* and 22*b*, and a fixed wire 26. In this embodiment, the guide rings 24 are equidistantly arranged along a centroid B with 2 mm intervals by attaching all five guide rings 24 to the fixed wire 26 with five respective anchors 28 (not shown). Therefore, the fixed wire 26 is terminated to five guide rings 24 in the first bendable segment 12. In other embodiments, the driving wires 22*a* and 22*b* are terminated on the guide ring 24 at a distal end of the bendable distal section 12, but not on the other four guide rings 24. By pushing and pulling the driving wires 22*a* and 22*b*, while holding the first fixed wire 26 in a fixed position, the bendable distal section 12 can bend three-dimensionally.

Additionally, the fixed wire 26 may be absent from an embodiment, which leads to greater flexibility in the bronchoscope 10. In the subject embodiment, the bronchoscope 10 has a consistent outer diameters (e.g., 3 mm) and identical inner diameters (e.g., 1.8 mm). The inner diameter forms the tool channel.

Embodiment 1: Difficulty Score for Robotic Bronchoscopy

Figure 2:
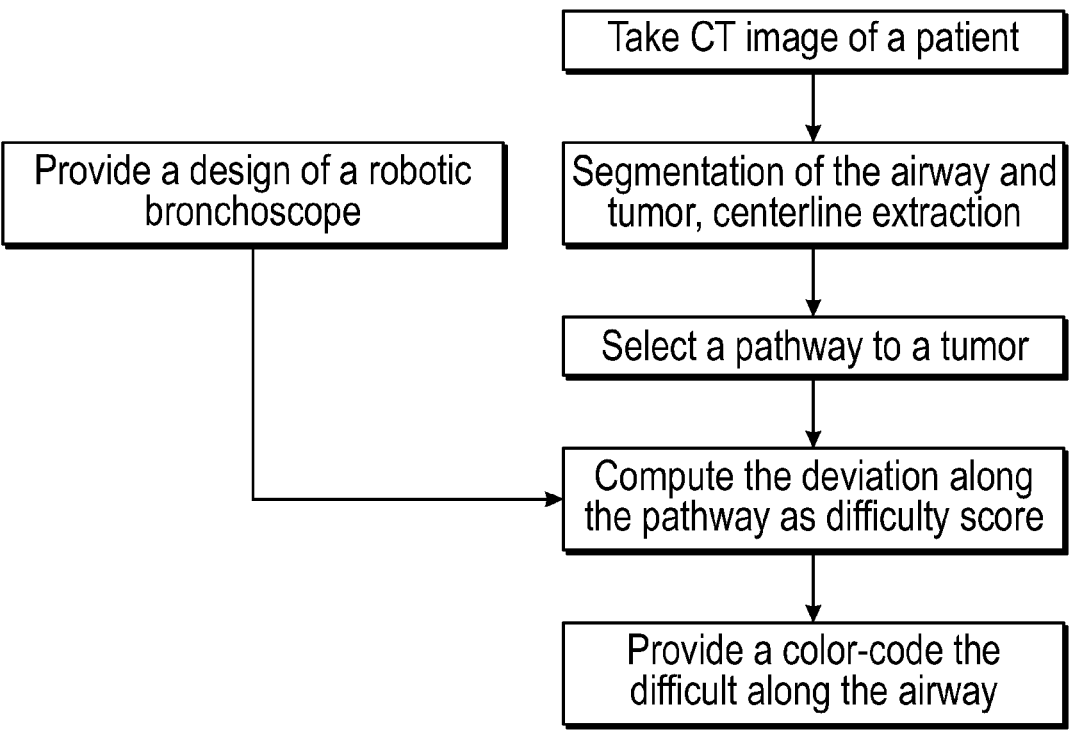
FIG. 2 is a flowchart depicting a method for employing the robotic medical device, according to one or more embodiments of the present subject matter.

FIG. 2 details an exemplary flowchart for employing the subject robotic bronchoscopy 10. A computer tomography ("CT") image of a patient is taken, by way of example we will focus on a lung cancer screening in this example. If a suspected tumor is found in the CT image, the airway and the tumor of the CT image of the patient are segmented, and the centerline of the segmented airway is extracted. An airway leading to the tumor is selected as the pathway for the three-section robotic bronchoscope 10 to be inserted. Then using the forward kinematics (see details below) under the constant-curvature model, the shape of the three-section robotic bronchoscope 10 is computed along the pathway. In this model, the shape of each section is determined by the direction of the tip of each section of the bronchoscope 10.

As the direction of the tip of the distal section of the bronchoscope 10, the direction of the tangential line of the centerline is used (see the steps below for further details). To decide the direction of the tip of the middle and proximal section, a follow-the-leader ("FTL") algorithm is applied. The FTL algorithm stores the direction of the tip of the distal section as a function of the insertion depth, and then the same value is applied as the direction of the tip of the middle and proximal sections to compute the shape of the middle and distal sections when the middle and distal sections reach at the same insertion depth.

FIG. 14 shows a Y-Z plan view of a bending state of the bending section 20 when the driving wires 22*a*, 22*b* and 22*c* are driven by a driving displacement $l_p$ on the +Z side in the Z-axis direction.

When θ denotes a change in angle of the distal member after driving and l denotes a length of the bending section 20 before driving, the bending section 20 bends in the Y-Z plane while maintaining a constant curvature. When $r_a$, $r_b$, and $r_c$ respectively denote curvature radii of the driving wires 22*a*, 22*b* and 22*c*, the following relationship can be obtained with reference to FIG. 14.

$$r_a \cdot \theta = l \tag{1}$$

$$r_b \cdot \theta = l + l_p \tag{2}$$

$$r_c \cdot \theta = l + l_p \tag{3}$$

Also, the distance between the three guide holes, displaced 120 degrees on each guide ring 24, projected in the Y-Z plane is 3r/2, and hence the following relationship can be obtained.

$$r_a = r_b - \frac{3r}{2} = r_c - \frac{3r}{2} \tag{4}$$

By using Expressions (1), (2), (3), and (4), the following relationship can be obtained.

$$\theta = \frac{2l_p}{3r} \tag{5}$$

The configuration above has been described such that the bending section 20 is bent in the Y-Z plane by driving the driving wires 22*b* and 22*c* on the +Z side in the Z-axis direction while the driving wire 22*a* is fixed. When the driving wires 22*b* and 22*c* are respectively driven on the +Z side in the Z-axis direction by the driving displacement $l_p$ and on the −Z side in the Z-axis direction by the driving displacement $l_p$ while the driving wire 22*a* is fixed, the bending section 20 can be bent in the X-Z plane. If the deformation in the X-Z plane is considered similarly to the deformation in the Y-Z plane, when θ denotes a change in angle of the distal member after driving, l denotes a length of the bending section 20 before driving, and $r_a$, $r_b$, and $r_c$ respectively denote curvature radii of the driving wires 22*a*, 22*b* and 22*c*, the following relational expression can be obtained.

$$r_a \cdot \theta = l \tag{6}$$

$$r_b \cdot \theta = l + l_p \tag{7}$$

$$r_c \cdot \theta = l - l_p \tag{8}$$

$$r_a = r_b - \frac{\sqrt{3}\,r}{2} \tag{9}$$

By using Expressions (6), (7), (8), and (9), the following relationship can be obtained:

$$\theta = \frac{2l_p}{\sqrt{3r}} \tag{10}$$

Further, the bending section 20 can be bent in a desirable plane containing the Z-axis, in accordance with a combination of the driving amounts of the driving wires 22b and 22c. To control the posture of the distal section 12, driving two of the three driving wires 22 is sufficient. In this case, the actuator coupled to the driving wires 22 that is not driven may not actually have a driving mechanism. Therefore, it is desirable to drive two driving wires 22 while not driving one driving wire, in order to reduce the space occupied by the wires. Also, if the direction in which the bronchoscope 10 is desired to be bent is previously determined, one of the three driving wires 22 may be driven while the remaining two driving wires 22 are not driven. Further, a mechanism that rotates the bronchoscope 10 around the Z-axis may be additionally provided, and the bending section 20 may be bent in a desirable direction by driving only one driving wire. In this case, two of the three driving wires 22 may be fixed. For example, the driving wires 22 that are not driven by the actuator may be fixed to the guide ring 24, and the driving wire 22 that is driven may slide with respect to the guide ring 24 without being fixed to the guide ring 24.

The guide ring 24 has a function of preventing the driving wires 22 from buckling when the bending section 20 is bent, and insuring a constant curvature of the bending section 20 by maintaining the interval between the driving wires 22. Thus, a large number of guide rings 24 arranged in the bending section 20 is desirable. On the other hand, if the driving wires 22 is driven to the −Z side in the Z-axis direction, the length of the driving wire 22 in the bending section 20 is decreased, and the interval between the guide rings 24 is decreased. Thus, the number of guide rings 24 is determined such that the guide rings 24 are arranged so as to not mechanically interfere with each other. Therefore, when 1 denotes a length of the bending section 20 before driving, $l_{pmax}$ denotes the maximum driving amount of the driving wires 22, $T_t$ is the thickness in the Z-axis direction of the distal section 12, $T_g$ is a thickness in the Z-axis direction of the guide ring 24, and $N_g$ is the number of guide rings 24 in the bending section 20, respective parameters are desirably designed to establish the following relationship.

$$l-l_{pmax} < T_t + T_g \cdot N_g \tag{11}$$

By fixing the guide rings 24 to one of the driving wires 22, a constant interval can be maintained between the guide ring 24 when the bending section 20 is bent, resulting in improvement of the driving reproducibility of the bending section 20. Also, the curvature within the bending section 20 can be maintained to be constant, and controllability of the posture of the bending section 20 at the driving of the driving wires 22 is improved. Further, by maintaining a constant interval between the neighboring guide rings 24, the guide rings 24 can be prevented from mechanically interfering with each other.

The forward kinematics are provided in the X-Z plane of a continuum robot detailed in FIGS. 15 and 16. The definition of symbols for equations provided below are: $l_n$: a length of an n-th bending section, $r_n$: a displacement from guide holes 8a, 8b, and 8c of a guide member of the n-th bending section to the center of the guide member, e: the number of bending sections of a robot, $\theta_n$: an angle of a distal end of the n-th bending section, $\theta_{refn}$: a target angle of the distal end of the n-th bending section, $l_{pn}$: a driving displacement of a wire of the n-th bending section, $x_{tn}$, $z_{tn}$: coordinates of the distal end of the n-th bending section, c: the total number of evaluation points of the robot, $x_i$, $z_i$: i-th coordinates when the robot is divided into a number c in the longitudinal direction, and $z_b$: a base displacement.

Kinematics, shown in FIG. 15, of the continuum robot in which the number of bending sections is n, are derived based on the following assumptions:

1. A wire is deformed only in a paper plane.
2. The wire is deformed with a constant curvature in each bending section.
3. Twisting deformation of the wire is not considered.
4. The wire is not deformed in the longitudinal direction.

First, Expression (5) becomes the following expression:

$$l_{p1} = \frac{3}{2} r_1 \theta_1 \tag{12}$$

Then, the relationship between the wire driving displacement $l_{pn}$ and the angle $\theta_n$ of the distal end of the n-th bending section is derived. In this case, it is assumed that n is 2 or larger. A bending relative angle of the n-th bending section, which is denoted as $\tilde{\theta}_n$ is defined as follows:

$$\tilde{\theta}_n = \theta_n - \theta_{n-1} \tag{13}$$

Then, when $x_{tn-1}$, $z_{tn-1}$ denote the origin, and a relative coordinate system $x_n$-$z_n$ in a $\theta_{n-1}$ direction and the direction orthogonal to that direction is plotted as shown in FIG. 8, the relationship between the driving displacement of the wire in the relative coordinate system $x_n$-$z_n$, which is denoted as $\tilde{l}_{pn}$ and the angle of the distal end of the first bending section, which is denoted as $\tilde{\theta}_n$ is expressed as follows:

$$\tilde{l}_{pn} = \frac{3}{2} r_n \tilde{\theta}_n \tag{14}$$

The wire driving displacement $l_{pn}$ of the n-th bending section is the sum total of displacements of wires for driving the n-th bending section in the relative coordinate system from the first to (n−1)th sections. The sum total is expressed as follows:

$$l_{pn} = \frac{3}{2} r_n (\tilde{\theta}_n + \tilde{\theta}_{n+1} + \dots + \tilde{\theta}_1) = r_n \theta_n \tag{15}$$

Accordingly, it is found that the angle $\theta_n$ of the distal end of the n-th bending section is determined only on the basis of the wire driving displacement $l_{pn}$, and the angle $\theta_n$ does not depend on the angle of the midway bending section.

Next, the relationship between the distal end angle and distal end coordinates of the n-th bending section is derived. The first bending section is considered as follows:

$$x_{t1} = \frac{l_1}{\theta_1}(1 - \cos\theta_1) \tag{16}$$

$$z_{t1} = \frac{l_1}{\theta_1}\sin\theta_1 \tag{17}$$

Then, the relationship between the distal end angle and the distal end coordinates of the n-th bending section is derived. In this case, it is assumed that n is 2 or larger. The coordinates of the distal end of the bending section in the relative coordinate system $x_n$–$z_n$, which are denoted as $\tilde{x}_{tn}$ and $\tilde{z}_{tn}$ are expressed as follows:

$$\tilde{x}_{tn} = \frac{l_n}{\theta_n}(1 - \cos\theta_n) \tag{18}$$

$$\tilde{z}_{tn} = \frac{l_n}{\theta_n}\sin\theta_n \tag{19}$$

Accordingly, the coordinates $x_{tn}$, $z_{tn}$ of the distal end in the absolute coordinate system are obtained as follows by using rotation transformation matrix.

$$\begin{bmatrix} x_{tn} \\ z_{tn} \end{bmatrix} = \begin{bmatrix} x_{t1} \\ z_b + z_{t1} \end{bmatrix} + \sum_{m=2}^{n} \begin{bmatrix} \cos\theta_{m-1} & \sin\theta_{m-1} \\ -\sin\theta_{m-1} & \cos\theta_{m-1} \end{bmatrix} \begin{bmatrix} \frac{l_m}{\theta_m}(1 - \cos\theta_m) \\ \frac{l_m}{\theta_m}\sin\theta_m \end{bmatrix} \tag{20}$$

Also, in the next term, the coordinates for dividing the entire robot into $\alpha$ times are used as evaluation points for an optimization algorithm. At this time, the total number of evaluation points is $c = \alpha e$. The coordinates $x_i$, $z_i$ of an i-th evaluation point are obtained as follows.

$$\begin{bmatrix} x_i \\ z_i \end{bmatrix} = \begin{bmatrix} \frac{l_1}{\left(\frac{R}{\alpha}\right)\theta_1}\left(1 - \cos\left(\frac{R}{\alpha}\right)\theta_1\right) \\ \frac{l_1}{\left(\frac{R}{\alpha}\right)\theta_1}\sin\left(\frac{R}{\alpha}\right)\theta_1 \end{bmatrix} + \begin{bmatrix} 0 \\ z_b \end{bmatrix} \quad (i < \alpha) \tag{21}$$

$$\begin{bmatrix} x_i \\ z_i \end{bmatrix} = \sum_{n=1}^{Q} \begin{bmatrix} x_{in} \\ z_{in} \end{bmatrix} \quad (i = n\alpha)$$

$$\begin{bmatrix} x_i \\ z_i \end{bmatrix} = \sum_{n=1}^{Q} \begin{bmatrix} x_{in} \\ z_{in} \end{bmatrix} + \begin{bmatrix} \cos\theta_Q & \sin\theta_Q \\ -\sin\theta_Q & \cos\theta_Q \end{bmatrix}$$

$$\begin{bmatrix} \frac{l_{Q+1}}{\left(\frac{R}{\alpha}\right)\theta_{Q+1}}\left(1 - \cos\left(\frac{R}{\alpha}\right)\theta_{Q+1}\right) \\ \frac{l_{Q+1}}{\left(\frac{R}{\alpha}\right)\theta_{Q+1}}\sin\left(\frac{R}{\alpha}\right)\theta_{Q+1} \end{bmatrix} + \begin{bmatrix} 0 \\ z_b \end{bmatrix}$$
$$(i = n\alpha + 1, \ \ldots, n\alpha + \alpha - 1)$$

In this case, Q, R are a quotient and a remainder, and are obtained from $Q = [i/\alpha]$, $R = i$ mod $\alpha$.

Below shows the detailed steps commencing with: the carina is set as the starting point of insertion (insertion depth=0); the direction of the tangential line of the centerline at $d_1$ from the carina (insertion depth=$d_1$) is set as the direction of the tip of the distal section at insertion depth=$d_1$; FTL algorithm sets the direction of the tip of middle section and proximal section; The shape of the bending sections (distal, middle, and proximal) of the robotic bronchoscope at insertion depth=$d_1$ is computed using the directions set at step 2 and 3.

As shown in FIG. 3, this computation assumes that the base of the proximal section is on the centerline of the airway; The deviation between the centerline of the pathway and the computed shape of the robotic bronchoscope is computed along the robotic bronchoscope as illustrated in FIG. 3; The difficulty score at insertion depth=$d_1$ is computed as the summation of the deviation along the robotic bronchoscope computed at step 5; Steps 2-6 are repeated for insertion depth of $d_2$, $d_3$ . . . until do is reached at the end of the desired pathway/target; and the difficulty score at each insertion depth is presented on a monitor (FIG. 4), here with color-coding along the pathway, we can symbolize degrees of difficulty.

As an example, FIG. 5 shows the selected pathway (solid lines) and the computed shape of the three-section robotic bronchoscope (broken lines) at every 10 mm of insertion depth.

Based on the difficulty score, physicians can estimate the time to finish the procedure by comparing with past procedures. In addition, if the difficulty score is large enough, the physicians can switch to alternative operations (open surgery or transthoracic needle aspiration) without performing bronchoscopy.

During robotic bronchoscopy, the maximal speed of inserting and bending the robotic bronchoscope may be decided based on the difficulty score as well. At location(s) having a higher difficulty score, the maximal speed of inserting and bending of the robotic bronchoscope may be adjusted down, for example, to minimize possible trauma or discomfort. By varying the speed based on the difficulty score, physicians can perform bronchoscopy more safely.

As mentioned, this embodiment assumes that the base of the proximal section is on the centerline. However, when the diameter of the airway is wide enough and there is a gap between the base of the proximal section and the inner wall of the airway, the assumption cannot be fully applied. In this case, the offset corresponding to the gap, shown in FIG. 6, is applied to account for the deviation between the centerline of the pathway and the computed shape of the robotic bronchoscope.

Embodiment 2: Difficulty Score to Select the Easiest Pathway from Multiple Pathways FIG. 7 provides an exemplary flowchart for enacting the bronchoscope according to this secondary embodiment. Similar to Embodiment 1, if a potential tumor is found in the CT image, here of a lung cancer screening, the airway and the tumor in the CT image of the patient are segmented, and the centerline of the segmented airway is extracted. Then using the forward kinematics under the constant-curvature model, the shape of the three-section continuum robot is computed along multiple pathways close to the tumor.

As mentioned in Embodiment 1, the deviation between the centerline of the pathway and the computed shape of the robotic bronchoscope is computed along the robotic bronchoscope as illustrated in FIG. 3, and summed along the robotic bronchoscope.

The summation of the deviation is used as the difficulty score at each insertion depth. The difficulty score for each pathway at each insertion depth is visually distinguishable, herein grey-scaled or preferably color-coded (see FIG. 8), to help a physician to select the easiest pathway to the tumor.

Embodiment 3: Difficulty Score to Select the Best Robotic Bronchoscope to Reach the Tumor FIG. 9 provides an exemplary flowchart for enacting the bronchoscope according this third embodiment. Similar to Embodiment 1, if a tumor is found in the CT image of lung cancer screening, the airway and the tumor of the CT image of the patient are segmented, and the centerline of the segmented airway is extracted. An airway leading to the tumor is selected as the pathway for a multi-section robotic bronchoscope to be inserted. In this third embodiment, a physician has three different options for the robotic bronchoscope with different bendable segments. For example, Design 1 has two bending sections, and the length of the two bending section are 10 mm and 15 mm, Design 2 has three bending sections, and the length of each section is 20 mm, and Design 3 has one bending section of 40 mm. Using the forward kinematics under the constant-curvature model, all three multi-section robotic bronchoscopes are computed along the pathway. Based on the deviations, the difficulty score of each design for the pathway is computed, and the difficulty score for each design of robotic bronchoscope is displayed (FIG. 10), here by preferably color-coding (grayscale in FIG. 10), the physician may select the best design to reach the tumor along the pathway.

Embodiment 4: Difficulty Score to Select the Best Catheter and Pathway to Reach the Tumor FIG. 11 shows the flowchart of this forth embodiment. The CT imaging and pathways are similar to previous embodiments, However, in this embodiment there are three pathways (A, B, and C) leading to a tumor and a physician has two different designs of robotic bronchoscope (Design 1 and 2), the difficulty score is computed for all possible six combinations of three pathways and two designs. The color-coded pathways are shown on a monitor to provide the best combination of pathway and design of the robotic bronchoscope (FIG. 12).

Embodiment 5: Optimization of Design of Robotic Bronchoscope Based on Difficulty Score FIG. 13 shows the flowchart for this embodiment. When a physician select a pathway leading to a tumor, a design of robotic bronchoscope is provided. The difficulty score of the pathway is computed using the design of the robotic bronchoscope. If the maximal and/or average score of the difficulty score along the pathway is larger than the pre-determined threshold, a different design of the robotic bronchoscope is provided. The design parameters of the robotic bronchoscope to be changed are the number of sections, the length of the section, and the diameter of the robotic scope. This process is repeated until the maximal and/or average score of the difficulty score is lower than the threshold, and/or lowest overall. Then the robotic bronchoscope which is best for the selected pathway is created, and used for bronchoscopy for this patient.

In instances where various robotic bronchoscopes are evaluated to determine the most beneficial pathway, the bronchoscope may consist of multiple interchangeable bendable bodies which are removably attached to the actuation unit. Thus drastically reducing the cost of the bendable medical apparatus, while allowing maximum flexibility to the end user in determining the best pathway, and associated bendable segment, to be used in reaching the target.

The invention claimed is:

1. A method for using a bendable medical apparatus comprising:

providing a computed tomography image of a subject;
  providing a bendable medical apparatus comprising:
    an actuator;
    a first bendable body which is bendable by the actuator; and
    a controller configured to send a control signal to the actuator for bending the first bendable body;
  mapping a first pathway for the first bendable body based on the computed tomography image of a subject;

determining a deviation of the first pathway for the first bendable body from a centerline of the mapped first pathway and a computed shape of the first bendable body; and
  assigning a first difficulty score for the first pathway based on a level of deviation of the first pathway.

2. The method of claim 1, wherein the first bendable body has at least two bendable segments, which are independently bendable by the actuator.

3. The method of claim 1, further comprising mapping a second pathway for the first bendable body and assigning the second pathway a second difficulty score.

4. The method of claim 3, further comprising mapping a third pathway for the first bendable body and assigning the third pathway a third difficulty score.

5. The method of claim 4, wherein the first pathway, the second pathway, and the third pathway are all pathways to a single target.

6. The method of claim 4, further comprising presenting the first difficulty score, the second difficulty score, and the third difficulty score.

7. The method of claim 2, wherein the first bendable body is removable and is configured to be exchanged for a second bendable body having at least two bendable segments, wherein at least one of the at least two bendable segments for the second bendable body has a different length than at least one of the at least two bendable segments of the first bendable body.

8. The method of claim 7, further comprising
  mapping a second pathway for the second bendable body;
  determining a deviation of the second pathway for the second bendable body; and
  assigning second difficulty score for the second pathway based on a level of deviation of the second pathway.

9. The method of claim 7, further comprising presenting the difficulty score and a second difficulty score.

10. The method of claim 7, wherein the first bendable body and the second bendable body have different overall lengths.

11. The method of claim 1, wherein an actuation speed of the actuator is adjustable to allow for rapid to slow advancement of the first bendable body.

12. The method of claim 1, wherein the bendable medical apparatus further comprises a display to relay the difficulty score for the pathway.

13. The method of claim 1, further comprising mapping multiple pathways for the bendable medical apparatus based on the computed tomography image of a subject.

14. The method of claim 13, wherein a difficulty score is assigned to each of the multiple pathways.

15. The method of claim 1, wherein the deviation of the pathway for the first bendable body from a centerline of the mapped pathway is computed using a constant-curvature model.

16. The method of claim 1, wherein a direction of a tangential line of the centerline of the mapped pathway is used to compute the shape of the first bendable body.

17. The method of claim 1, wherein the shape of the first bendable body is computed under assumptions that: (1) a direction of a tangential line of the centerline of the pathway at a depth (d) from a carina is set as a direction of the tip of a distal section of the first bendable body at insertion depth=d, (2) a base of a proximal section is on the centerline of the pathway, and (3) a follower section is controlled by a follow-the-leader (FTL) algorithm.

18. The medical apparatus of claim 1, further comprising a sheath having an outer wall covering at least the first bendable body.

19. The method of claim 1, further comprising providing instructions for inserting the bendable medical apparatus into the subject, wherein the instructions provide for an adjustment of the first bendable body, a selection of a second bendable body, a selection of a pathway from one from a set of multiple pathways, or an adjustment of the control signal that is based on the difficulty score.

20. A method for treating a subject, comprising:
providing a computed tomography image of the subject;
providing a bendable medical apparatus comprising:
an actuation;
a first bendable body which is bendable by the actuation; and
a controller configured to send a control signal to the actuation for bending the first bendable segment;
mapping a pathway for the first bendable body based on the computed tomography image of a subject;

determining a deviation of the pathway for the first bendable body from a centerline of the mapped pathway and a computed shape of the first bendable body;
assigning a difficulty score for the pathway based on a level of deviation of the pathway; and
providing instructions for inserting the first bendable body into the subject, wherein the instructions provide for an adjustment of the first bendable body, a selection of a second bendable body, a selection of a pathway from one from a set of multiple pathways, or an adjustment of the control signal that is based on the difficulty score to treat the subject.

21. The method of claim 20, wherein the first bendable body has at least two bendable segments, which are independently bendable by the actuator.

22. The method of claim 20, wherein the step of using the difficulty score to treat the subject comprises: selecting a bendable body, selecting a pathway, and/or selecting an insertion speed.

* * * * *